United States Patent
Patterson et al.

(10) Patent No.: US 11,122,831 B2
(45) Date of Patent: Sep. 21, 2021

(54) NUTRACEUTICAL FORMULATION FOR MITIGATING LOSS OF BONE AND FACILITATING BONE GROWTH

(71) Applicants: Benjamin Patterson, Findlay, OH (US); Thomas Zaciewski, Findlay, OH (US)

(72) Inventors: Benjamin Patterson, Findlay, OH (US); Thomas Zaciewski, Findlay, OH (US)

(*) Notice: Subject to any disclaimer, the term of this patent is extended or adjusted under 35 U.S.C. 154(b) by 0 days.

(21) Appl. No.: 16/545,010

(22) Filed: Aug. 20, 2019

(65) Prior Publication Data

US 2020/0054059 A1    Feb. 20, 2020

Related U.S. Application Data

(60) Provisional application No. 62/719,870, filed on Aug. 20, 2018.

(51) Int. Cl.
| | |
|---|---|
| *A61K 36/31* | (2006.01) |
| *A23L 33/105* | (2016.01) |
| *A61K 47/46* | (2006.01) |
| *A61K 36/87* | (2006.01) |
| *A61K 36/736* | (2006.01) |
| *A61K 36/07* | (2006.01) |

(52) U.S. Cl.
CPC ............ *A23L 33/105* (2016.08); *A61K 36/07* (2013.01); *A61K 36/31* (2013.01); *A61K 36/736* (2013.01); *A61K 36/87* (2013.01); *A61K 47/46* (2013.01)

(58) Field of Classification Search
None
See application file for complete search history.

(56) References Cited

U.S. PATENT DOCUMENTS

| | | | | |
|---|---|---|---|---|
| 2010/0215783 | A1* | 8/2010 | McNeary | A61K 36/45 424/732 |
| 2015/0216918 | A1* | 8/2015 | Nair | A61P 1/12 424/195.15 |
| 2016/0192689 | A1* | 7/2016 | Horn | A23L 33/22 424/439 |
| 2019/0200665 | A1* | 7/2019 | Donnelly | C11B 9/0003 |

OTHER PUBLICATIONS

Naghii M. et al. The Boron Content of Selected Foods and the Estimation of its Daily Intake Among Free Living Subjects. J of the American College of Nutrition 15(6)614-619, 1996. (Year: 1996).*

* cited by examiner

*Primary Examiner* — Ralph J Gitomer
(74) *Attorney, Agent, or Firm* — Jacob M. Ward; Ward Law Office LLC

(57) ABSTRACT

A nutraceutical formulation used to militate against bone loss, while also facilitating bone growth, is disclosed herein. The nutraceutical formulation used to therapeutically treat humans includes kale, broccoli, mushroom, raisin, and prune. The nutraceutical formulation also omits ingredients that would otherwise diminish bone density or inhibit the inhibitory effects of the other ingredients in mitigating bone loss.

15 Claims, No Drawings

NUTRACEUTICAL FORMULATION FOR MITIGATING LOSS OF BONE AND FACILITATING BONE GROWTH

CROSS REFERENCE TO RELATED APPLICATIONS

This application claims the benefit of U.S. Provisional Application Ser. No. 62/719,870, filed on Aug. 20, 2018. The entire disclosure of the above application is hereby incorporated herein by reference.

FIELD

The present disclosure relates to nutraceuticals and, more particularly, to a nutraceutical formulation containing natural ingredients for use in mitigating loss of bone and facilitating bone growth.

BACKGROUND

As a result of the aging process, bone deteriorates in composition, structure and function, which may lead to osteopenia or osteoporosis. Bone is a dynamic organ, undergoing a continual self-regeneration process called remodeling. Remodeling is a cellular process that removes old bone and replaces it with new bone. With aging this balance shifts in a negative direction, favoring greater bone resorption and less bone formation. This combination of bone mass deficiency and reduction in strength ultimately may result in osteopenia or osteoporosis and fractures. Aging in combination with intrinsic and extrinsic factors accelerates the decline in density or bone mass that can lead to osteopenia or osteoporosis.

Causes of bone loss may include diet, smoking, age-related hormone changes, and certain diseases and medications. Women are most at risk. Typically, there are no symptoms, unless the condition progresses to osteoporosis. Symptoms of osteoporosis include back pain, loss of height, a stooped posture, and easily fractured bones. Treatments include medication to protect bone mass, dietary changes, and exercise.

To combat bone loss, a doctor may prescribe bisphosphonates, slowing bone degeneration by turning off osteoclasts, cells that break down bone, while allowing the osteoblasts to continue making new bone. In some cases, bisphosphonate pills can irritate the lining of the esophagus and stomach, causing gastritis and acid reflux. There are also recommended dietary changes for those suffering from bone loss that may limit foods in oxalate, sugar, and alcohol as these ingredients have been shown to be linked to bone loss.

There is a continuing need for a nutraceutical formulation that contains natural ingredients that may mitigate bone loss. Desirably, the nutraceutical formulation may be administered without causing the side effects associated with the use of bisphosphonates.

SUMMARY

In concordance with the instant disclosure, a nutraceutical formulation that contains ingredients that may mitigate bone loss, and which may be administered without causing the side effects associated with the use of bisphosphonates, has surprisingly been discovered.

Certain natural ingredients have been found useful for militating against bone degradation when provided in appropriate concentrations. Nutraceutical supplements made from combinations of these natural ingredients are useful for supplying these ingredients in effective amounts, especially when prevention of bone loss, and increasing bone density is desirable.

In one embodiment, a nutraceutical formulation is a whole food supplement including kale, broccoli, mushroom, raisin, and prune.

In an exemplary embodiment, the nutraceutical formulation is a whole food supplement. The active ingredients are dehydrated or freeze-dried natural ingredients, and include kale, broccoli, mushroom, raisin, and prune. Specifically, the calcium in the kale and broccoli, vitamin D in the mushroom, vitamin K in the kale, broccoli, and prune, boron in the raisin and prune, potassium in the mushroom, raisin, and prune, magnesium in the raisin and broccoli, and vitamin C in the kale and broccoli, all function synergistically to mitigate bone loss and encourage new bone formation. The formulation is orally ingested in a variety of dosage forms, for example, as a drinkable powder or in the form of a capsule or tablet.

In certain embodiments, natural ingredients to mitigate bone loss, and facilitate new bone growth includes foods rich in calcium (e.g., kale, broccoli), vitamin D (e.g., mushroom), vitamin K (e.g., kale, broccoli, prune), boron (e.g., raisin, prune), potassium (e.g., mushroom, raisin, prune), magnesium (e.g., raisin, broccoli), and vitamin C (e.g., kale, broccoli).

Calcium is well established in the scientific community as an important mineral for maintaining healthy bone growth and density. Bone is a composite material made of mineral crystals bound to protein. The mineral phase of bone consists of small crystals containing calcium and phosphate, called hydroxyapatite. This mineral is bound in an orderly manner to a protein matrix that is made up largely of a collagen. The combination of hydroxyapatite and collagen form the building blocks of the human skeleton. Bones also function as a storage facility for calcium used throughout the body. If a patient's diet does not include enough calcium to replace what is used, the body will leach calcium from the bones, increasing the risk of fracture. Accordingly, calcium aids in the preservation of existing bone, while contributing to new bone creation.

Further research has shown vitamin D is essential for bone formation and densification. Vitamin D is a secosteriod hormone essential for calcium absorption and bone mineralization, which is associated with bone mineral density. It is well-established that prolonged and severe vitamin D deficiency leads to osteomalacia in adults. Moreover, inadequate vitamin D intake over long periods of time may lead to bone demineralization. Vitamin D deficiency causes reduced calcium absorption and ultimately the release of calcium from the bones in order to maintain circulating calcium concentrations. Consequentially, vitamin D has been shown to reduce bone resorption and strengthen bone density.

Additionally, various studies suggest that vitamin K militates against the loss of bone and promotes the growth of new bone. Adequate amounts of vitamin K are needed in order to activate osteocalcin—a protein that is responsible for binding calcium ions to the matrix of bone. Vitamin K is also needed to activate Matrix Gla Protein (MGP), another protein that is associated with the formulation of cartilage and bone. By activating proteins associated with bone regeneration, vitamin K has been shown to stimulate bone growth.

Further research suggests boron is essential for healthy bones. Boron plays an important role in osteogenesis, and its deficiency has been shown to adversely impact bone development and regeneration. Boron influences the production and activity of steroid hormones, actions which prevent calcium loss and bone demineralization. Boron supplementation has repeatedly been shown to markedly reduce urinary excretion of both calcium and magnesium and to optimize calcium absorption. Supplementation with boron has also repeatedly been shown to stimulate bone growth in animals and humans.

Potassium has also been found to be key mineral for bone growth. Potassium neutralizes bone-depleting metabolic acids, and significantly reduces the excretion of calcium and acid in urine.

Numerous scientific studies suggest magnesium is required for forming new calcium crystals. If magnesium levels are low, abnormal bone crystal formation can result. Even mild magnesium deficiency is a leading risk factor for osteoporosis. As with calcium, the majority of the body's reserves of magnesium are held in the bone. The bones act as a storage reservoir, transferring magnesium into the blood stream in times of need. Adequate magnesium consumption supports the formation of calcium crystals, increasing the rigidity of the bone structure.

Vitamin C is needed for normal bone development and the formation of collagen. Vitamin C reduces oxidative stress, protecting bones against inflammation. Inflammation fosters bone resorption, which leaches calcium away from the bones, thereby structurally weakening the skeleton. Consequentially, vitamin C slows bone resorption, increasing bone density.

The nutraceutical formulation according to the present disclosure is particularly useful for militating against or preventing bone loss, and encouraging the formation of new bone, while improving bone density. In furtherance of this objective, the nutraceutical formulation is also limited to only natural ingredients that help mitigate bone loss. Certain ingredients that would otherwise diminish bone density or interfere with the prevention of bone loss are omitted from the formulation.

Omitted ingredients may include foods rich in oxalate (e.g., beets, spinach, swiss chard, cranberries, bran, soy products, parsley, rhubarb, celery, most nuts and nut butters, tea, cocoa, etc.), sugars (e.g., high fructose consumption), sodium, animal protein, caffeine, carbonated beverages, phytates (e.g., legumes/beans), alcohol (e.g., beer, wine spirits) and hydrogenated oils.

In an additional embodiment, a nutraceutical formulation may be advantageously manufactured using whole food ingredients. Whole food ingredients contain thousands of nutrients (for example, an apple contains >10,000 vitamins, phytochemicals, and nutrients), so while each whole food ingredient within the nutraceutical formulation is chosen for specific nutrients, the whole food ingredients contain additional nutrients that provide added benefits to the body. The additional nutrients synergistically enhance the efficacious nature and bioavailability of the nutraceutical formulation.

Additionally, whole food nutrients have been shown to increase overall alkalinity in the body, which is beneficial for many reasons, including a reduction in cancer, kidney stones, and most chronic diseases. Furthermore, because the nutraceutical formulation is manufactured using whole food ingredients, and not synthetic formulations, the user will be much less likely to overdose on vitamins from the nutraceutical formulation, compared to vitamins in other synthetic formulations.

Further areas of applicability will become apparent from the description provided herein. It should be understood that the description and specific examples are intended for purposes of illustration only and are not intended to limit the scope of the present disclosure.

DETAILED DESCRIPTION

The following description is merely exemplary in nature and is not intended to limit the present disclosure, application, or uses.

The terminology used in the specification provided herein below is hereby defined to include similar and/or equivalent terms, and/or alternative embodiments that would be considered obvious to one skilled in the art given the teachings of the present patent application. Additionally, the words "a," "an," and "one" are defined to include one or more of the referenced item unless specifically stated otherwise. Also, the terms "have," "include," "contain," and similar terms are defined to mean "comprising" unless specifically stated otherwise.

Except where otherwise expressly indicated, all numerical quantities in this description are to be understood as modified by the word "about" in describing the broadest scope of the technology. When describing weight percentages of various ingredients in formulations of the present disclosure, as set forth hereinbelow, the term "about" is hereby defined to mean within plus or minus five weight percent (±5 wt %) by weight relative to a total weight of the formulation.

The present disclosure is directed to a nutraceutical formulation. The nutraceutical formulation may include kale, broccoli, mushroom, raisin, and prune. Each of these natural ingredients may be dehydrated or freeze-dried and powdered or granulated prior to being incorporated into the nutraceutical formulation.

For example, the natural ingredients may be powdered or granulated to a particle size between about 10 microns and about 300 microns, and more particularly between about 100 microns and about 200 microns. However, one of ordinary skill in the art may select other suitable particle sizes, including particle sizes adapted to facilitate water solubility of the nutraceutical formulation as described further herein below, as desired.

Furthermore, each of these natural ingredients may be substantially evenly mixed together according to conventional techniques to provide the nutraceutical formulation for convenient end use, as described further herein.

In a most specific embodiment, the nutraceutical formulation may be manufactured using whole food non-GMO ingredients. In particular, each of the kale, the broccoli, the mushroom, the raisin, and the prune, may be processed from whole food ingredients. However, other suitable forms of the ingredients may be chosen as desired. Additionally, each of these natural ingredients may be substantially evenly mixed together according to conventional techniques to provide the nutraceutical formulation for convenient end use, as described further herein. It should be understood that the powdered or granulated form of the natural ingredients facilitates flowability and mixability, and results in a substantially homogenous mixture of the natural ingredients for end use.

In particular examples, the natural ingredients are provided in a dosage form suitable for oral administration, including one or more tablets or artificial capsules, a manufactured or compounded liquid or slurry form, or as a manufactured powder or granulate. As a nonlimiting example, the powder or granulate form of the nutraceutical formulation may be water soluble. In particular, the nutraceutical formulation may be ground to, or otherwise provided in, a particle size that is adapted to naturally dissipate and dissolve within an aqueous medium. It should be appreciated that where the powdered or granulated ingredients of the nutraceutical formulation are dehydrated, the ingredients will furthermore more readily absorb water and dissolve in the aqueous medium, especially in comparison to synthetic vitamin alternatives. One of ordinary skill in the art may also select other suitable dosage forms within the scope of the present disclosure.

It should be appreciated that the capsule dosage form for the nutraceutical formulation may be preferred. Where provided in a capsule dosage form, the artificial capsules may be single-piece or two-piece manufactured bodies for encapsulation of the formulation. As further non-limiting examples, suitable ingredients for the manufactured capsules may include wax, cellulose (including, for example, Hypromellose or HPMC, and sometimes referred to as "veggie capsule"), starches, gelatin, pullulan/tapioca, and combinations thereof. Other suitable ingredients for capsules of the present disclosure may also be employed, as desired.

Other ingredients can be included, such as various excipients, including one or more antiadherents, binders, coatings, disintegrants, flavors, colors, lubricants, glidants, sorbents, preservatives, and sweeteners. Excipient examples include one or more of hypromellose, rice concentrate, rice flour, magnesium stearate, cellulose, inulin, and silicon dioxide. One of ordinary skill in the art may also select other suitable dosage forms and capsule types within the scope of the present disclosure.

In a more particular embodiment, the excipient may be rice concentrate, and the rice concentrate may be present in the nutraceutical formulation in a minor concentration relative to the other ingredients. In a most particular embodiment, the rice concentrate may be NU-FLOW® concentrate, which is commercially available from RIBUS, Inc. of St. Louis, Mo.

For example, the rice concentrate excipient may be present in a concentration ranging from less than about one weight percent (≤wt %) to about six weight percent (6 wt %), more particularly from about two weight percent (2 wt %) to about four weight percent (4 wt %), and most particularly to about two percent (3 wt %), each by weight relative to the total weight of the nutraceutical formulation. The Nu-FLOW® excipient has been found to provide anti-caking properties when used with the other ingredients described herein, which is beneficial during the manufacturing and mixing of the nutraceutical formulation of the present disclosure.

Kale has been found useful for the prevention of bone loss due to the presence of vitamin K, calcium, vitamin C and other antioxidants that may help shield bones from oxidative damage. For example, the kale may be present in a concentration ranging from about 14 to about 34 weight percent, more particularly about 19 percent to about 29 percent, and most particularly about 24 percent, each by weight relative to the total weight of the nutraceutical formulation. A skilled artisan may also select other suitable concentrations for the kale component, as desired.

Broccoli has been found useful for the prevention of bone loss. While not being bound to any particular theory, it is believed that the broccoli militates against bone loss, while facilitating bone growth, due to the presence of vitamin K, calcium, magnesium, and other antioxidants that may help shield bones from oxidative damage. For example, the broccoli may be present in a concentration ranging from about 14 to about 34 weight percent, more particularly about 19 percent to about 29 percent, and most particularly about 24 percent, each by weight relative to the total weight of the nutraceutical formulation. A skilled artisan may also select other suitable concentrations for the broccoli component, as desired.

Mushroom has also been found useful in the prevention of bone loss. While not being bound to any particular theory, it is believed that the mushroom militates against bone loss, while enhancing bone density. In exemplary embodiments, the mushroom may be a Maitake mushroom; however, other suitable types and varieties of mushroom may also be used, as desired. In particular, suitable mushrooms have been found to contain vitamin D, and potassium, which are believed to improve bone density. For example, the mushroom may be present in a concentration ranging from about 14 to about 34 weight percent, more particularly about 19 percent to about 29 percent, and most particularly about 24 percent, each by weight relative to the total weight of the nutraceutical formulation. A skilled artisan may also select other suitable concentrations for the mushroom component, as desired.

Raisins or dried grapes, have been found useful in the prevention of bone loss, while also stimulating bone growth and increasing bone density. While not being bound to any particular theory, it is believed that the raisin militates against bone loss due to the presence of boron, magnesium, and other antioxidants that may help shield bones from oxidative damage. For example, raisins may be present in a concentration ranging from about 5 to about 25 weight percent, more particularly about 10 percent to about 20 percent and most particularly about 15 percent, each by weight relative to the total weight of the nutraceutical formulation. A skilled artisan may also select other suitable concentrations for the raisin component, as desired.

Prunes have been found useful in the prevention of bone loss, while facilitating bone growth. Prunes are rich in nutrients vital for bone health, including vitamin K, potassium, and boron, along with chlorogenic acid and other antioxidants that may help shield bones from oxidative damage. For example, prunes may be present in a concentration ranging from about 1 percent to about 120 percent weight percent, more particularly about 5 to about 15 percent and most particularly about 10 percent, each by weight relative to the total weight of the nutraceutical formulation. A skilled artisan may also select other suitable concentrations for the prune component, as desired.

In an exemplary embodiment, as a non-limiting example, the formulation may include 187.5 mg of Organic Non-GMO Kale, 187.5 mg Organic Non-GMO Broccoli, 187.5 mg of Organic Non-GMO Mushroom (Maitake), 112.5 mg of Organic Non-GMO Raisins, Organic Non-GMO Prune 75 mg, 130 mg Hypromellose (e.g., veggie capsule), 20 mg rice concentrate (as an excipient) for a total 900 mg/capsule. However, any other suitable dosage quantity of the ingredients may be selected by a skilled artisan within the scope of the present disclosure.

The aforementioned natural ingredients may be dried, ground, and mixed together by conventional techniques. Thereafter, the powder mixture may be pressed and formed into tablets, or placed in capsules, for oral administration.

It is further believed that the aforementioned natural ingredients, when used in combination in the concentrations described herein, may behave synergistically to mitigate the loss of bone in users to whom the nutraceutical formulation is administered on a consistent and regular basis. For example, whole food products, and particularly kale, broccoli, mushroom, raisin, and prune, contain thousands of nutrients that can provide added benefits to the body and function synergistic to increase alkalinity and antioxidant levels within the user.

The present disclosure is not only defined by the ingredients present in the nutraceutical formulation, but also by ingredients purposely omitted or avoided. It should be appreciated that these omitted ingredients may hinder the prevention of bone loss. These ingredients include, spinach, swiss chard, and most nuts (due to the presence of oxalate), as well as legumes (due to the presence of phytates). Other non-desirable ingredients include those which contribute to inflammation and bone loss such as excess sugars, animal proteins, hydrogenated oils, caffeine, and alcohol. One of ordinary skill in the art may also determine other such ingredients to be omitted, and particularly ingredients that may otherwise contribute to bone loss, within the scope of the present disclosure.

As may be presented herein, the language "consisting essentially of" is meant to limit the scope of the claim to the specified materials that do not materially affect the basic and novel characteristics of the nutraceutical formulation. It should be appreciated that ingredients rich in oxalate, sugar, sodium, animal protein, caffeine, hydrogenated oils, and alcohol, have been shown to materially affect the basic and novel characteristics of the nutraceutical formulation by inhibiting the treatment and prevention of bone loss. Thus, the nutraceutical formulation consisting essentially of kale, broccoli, mushroom, raisin, and prune, excludes ingredients rich in oxalate, sugar, sodium, animal protein, caffeine, hydrogenated oils, and alcohol, which may materially affect the basic and novel characteristics of the nutraceutical formulation.

Additionally, as may be presented in the claims below, the language "consisting of" is intended to exclude any ingredient not specified in the claim. Accordingly, the nutraceutical formulation consisting of kale, broccoli, mushroom, raisin, and prune, and rice concentrate includes only those ingredients.

EXAMPLE

In one example, the nutraceutical formulation, including kale leaf powder, broccoli powder, mushroom powder, raisin powder, prune powder, and rice concentrate is administered to patients in a daily oral dose of about 1540 mg (not including any weight contributed by capsule ingredients). In particular, the dosage amounts of kale, broccoli, mushroom, raisin, prune, and rice concentrate are shown below in TABLE 1.

TABLE 1

Dosage of Nutraceutical Formulation

| Ingredients | Weight |
| --- | --- |
| Kale Powder | 375 mg |
| Broccoli Powder | 375 mg |
| Mushroom Powder | 375 mg |
| Raisin Powder | 225 mg |
| Prune Powder | 150 mg |
| Rice concentrate | 40 mg |
| TOTAL | 1540 mg |

The nutraceutical formulation, as shown in TABLE 1 above, will be administered daily to a patient. A dual energy x-ray absorptiometry (DEXA) scan may be performed prior to administration of the nutraceutical formulation, and during the administration of the nutraceutical formulation. The DEXA scan measures bone mineral density in the patient.

In particular, while administering the daily dose of the nutraceutical formulation of TABLE 1 above, the DEXA scan is expected to show an increase in the bone density levels of the patient. Advantageously, increased bone density may militate against pathological fractures of the bones. Further, increased bone density may militate against or alleviate bone pain symptoms stemming from osteoporosis and osteopenia.

While administering the daily dose of the nutraceutical formulation shown above in TABLE 1, the patient's blood may be tested periodically. In particular, where performing the blood testing, the medical professional will perform a microscopic exam, and analyze the calcium levels and the vitamin D levels within the blood. The calcium is measured using a metabolic blood panel, and vitamin D levels are measured using a 25-hydroxy vitamin D blood test.

While administering the daily dose of the nutraceutical formulation shown above in TABLE 1, the blood test is expected to show an increase in calcium levels in the blood. Calcium is important for maintaining healthy bone growth and density. Bones also function as a storage facility for calcium used throughout the body. If the patient's diet does not include enough calcium to replace what is used, the body will leach calcium from the bones, increasing the risk of fracture. Accordingly, an increase of calcium in the blood supply aids in the preservation of existing bone, while contributing to new bone creation.

While administering the daily dose of the nutraceutical formulation shown above in TABLE 1, the blood test is expected to show an increase in vitamin D levels in the blood. Vitamin D is essential for bone formation and densification. Vitamin D is required for calcium absorption and bone mineralization, which is associated with bone mineral density. Vitamin D deficiency leads to osteomalacia and demineralization. Vitamin D deficiency causes reduced calcium absorption and ultimately the release of calcium from the bones in order to maintain circulating calcium concentrations. Consequentially, an increase in blood vitamin D levels will strengthen bone density and militate against osteomalacia.

Advantageously, the nutraceutical formulation of the present disclosure may militate against or prevent bone loss, and encourage the formation of new bone, while improving bone density through regular or daily administration of the recited whole foods, and the associated nutrients naturally found therein in small amounts, into the body and blood stream over time. Since the ingredients of the present nutraceutical formulation are only dried natural food ingredients, and not mega-dosed synthetic and/or fragmented vitamins, etc. the patient cannot overdose on the nutraceutical formulation. Additionally, patients that cannot be administered capsules can either purchase the nutraceutical formulation in bulk powdered form or open the capsules and deposit the nutraceutical formulation into their mouths or into water and drink it in a dissolved or slurry form.

While certain representative embodiments and details have been shown for purposes of illustrating the invention, it will be apparent to those skilled in the art that various changes may be made without departing from the scope of the disclosure, which is further described in the following appended claims.

What is claimed is:

1. A nutraceutical formulation for mitigating loss of bone and facilitating bone growth, consisting essentially of a homogenous mixture of:

freeze dried kale powder;
freeze dried broccoli powder;
freeze dried mushroom powder;
freeze dried raisin powder;
freeze dried prune powder; and
a rice based excipient,
wherein each of the powders has a particle size between about 10 microns and about 300 microns, and
wherein the formulation omits spinach, swiss chard, nuts, legumes, animal proteins, hydrogenated oils, caffeine, and alcohol.

2. The nutraceutical formulation of claim 1, wherein the excipient is present in a concentration of about 3 percent by weight relative to a total weight of the nutraceutical formulation.

3. The nutraceutical formulation of claim 1, wherein the kale is present in a concentration ranging from about 14 percent to about 34 percent by weight relative to a total weight of the nutraceutical formulation.

4. The nutraceutical formulation of claim 1, wherein the kale is present in the nutraceutical formulation in a concentration of about 24 percent by weight relative to a total weight of the nutraceutical formulation.

5. The nutraceutical formulation of claim 1, wherein the broccoli is present in a concentration ranging from about 14 percent to about 34 percent by weight relative to a total weight of the nutraceutical formulation.

6. The nutraceutical formulation of claim 1, wherein the broccoli is present in a concentration of about 24 percent by weight relative to a total weight of the nutraceutical formulation.

7. The nutraceutical formulation of claim 1, wherein the mushroom is present in a concentration ranging from about 14 percent to about 34 percent by weight relative to a total weight of the nutraceutical formulation.

8. The nutraceutical formulation of claim 1, wherein the mushroom is present in a concentration of about 24 percent, by weight relative to a total weight of the nutraceutical formulation.

9. The nutraceutical formulation of claim 1, wherein the raisin is present in a concentration ranging from about 5 percent to about 25 percent, by weight relative to a total weight of the nutraceutical formulation.

10. The nutraceutical formulation of claim 1, wherein the raisin is present in a concentration of about 15 percent, by weight relative to a total weight of the nutraceutical formulation.

11. The nutraceutical formulation of claim 1, wherein the prune is present in a concentration ranging from about 1 percent to about 20 percent, by weight relative to a total weight of the nutraceutical formulation.

12. The nutraceutical formulation of claim 1, wherein the prune is present in a concentration of about 10 percent, by relative to a total weight of the nutraceutical formulation.

13. The nutraceutical formulation of claim 1, wherein the kale is present in a concentration of about 24 percent, the broccoli is present in a concentration of about 24 percent, the mushroom is present in a concentration of about 24 percent, the raisin is present in a concentration of about 15 percent, the prune is present in a concentration of about 10 percent, and the binder rice based excipient is present in a concentration of about 3 percent, each by weight relative to a total weight of the nutraceutical formulation.

14. The nutraceutical formulation of claim 1, wherein the mushroom is maitake mushroom.

15. A nutraceutical formulation for mitigating loss of bone and facilitating bone growth, consisting of a homogenous mixture of:
freeze dried kale powder;
freeze dried broccoli powder;
freeze dried mushroom powder;
freeze dried raisin powder;
freeze dried prune powder; and
a rice based excipient,
wherein each of the powders has a particle size between about 10 microns and about 300 microns.

* * * * *